(12) United States Patent
Nash et al.

(10) Patent No.: US 6,375,665 B1
(45) Date of Patent: Apr. 23, 2002

(54) APPARATUS AND METHOD FOR DISSECTING AND RETRACTING ELONGATE STRUCTURES

(75) Inventors: Michael F. Nash, Danville; Gary Ashley Stafford, Hayward, both of CA (US)

(73) Assignee: General Surgical Innovations, Inc., Norwalk, CT (US)

( * ) Notice: Subject to any disclaimer, the term of this patent is extended or adjusted under 35 U.S.C. 154(b) by 0 days.

(21) Appl. No.: 09/687,344

(22) Filed: Oct. 12, 2000

Related U.S. Application Data

(60) Division of application No. 09/187,879, filed on Nov. 6, 1998, now Pat. No. 6,179,854, which is a continuation-in-part of application No. 08/927,371, filed on Sep. 9, 1997, now Pat. No. 5,893,866, which is a continuation-in-part of application No. 08/815,398, filed on Mar. 10, 1997, now abandoned, which is a continuation-in-part of application No. 08/688,044, filed on Jul. 29, 1996, now abandoned, which is a continuation-in-part of application No. 08/447,124, filed on May 22, 1995, now Pat. No. 5,702,417.

(51) Int. Cl.[7] .............................................. A61M 29/00
(52) U.S. Cl. ........................................ 606/192; 606/190
(58) Field of Search ................................ 606/190, 192, 606/195, 198, 159–191, 194, 108; 600/204, 207; 604/102.02, 103.01, 103.07

(56) References Cited

U.S. PATENT DOCUMENTS

| 4,312,353 A | 1/1982 | Shahbabian ................ 128/344 |
| 4,493,711 A | 1/1985 | Chin et al. .................. 604/271 |
| 4,779,611 A | 10/1988 | Grooters et al. ............... 128/4 |
| 4,932,959 A | 6/1990 | Horzewski et al. ......... 606/194 |
| 5,032,113 A | 7/1991 | Burns ........................... 604/96 |
| 5,183,463 A | 2/1993 | Debbas ........................ 604/98 |
| 5,188,630 A | 2/1993 | Christoudias ................. 606/1 |
| 5,197,971 A | 3/1993 | Bonutti ....................... 606/192 |
| 5,269,753 A | 12/1993 | Wilk ............................. 604/49 |
| 5,307,814 A | 5/1994 | Kressel et al. ............ 128/653.5 |
| 5,331,975 A | 7/1994 | Bonutti ....................... 128/898 |
| 5,346,504 A | 9/1994 | Ortiz et al. ................. 606/192 |
| 5,359,995 A | 11/1994 | Sewell, Jr. .................... 128/20 |
| 5,373,840 A | 12/1994 | Knighton ......................... 128/4 |
| 5,383,889 A | 1/1995 | Warner et al. .............. 606/192 |
| 5,391,178 A | 2/1995 | Yapor .......................... 606/192 |
| 5,425,357 A | 6/1995 | Moll et al. ..................... 128/20 |
| 5,454,365 A | 10/1995 | Bonutti ....................... 600/204 |
| 5,464,394 A | 11/1995 | Miller et al. ................ 606/194 |
| 5,496,345 A | 3/1996 | Kieturakis et al. .......... 606/192 |
| 5,514,153 A | 5/1996 | Bonutti ....................... 606/190 |
| 5,601,589 A | 2/1997 | Fogarty et al. ............. 606/192 |
| 5,634,394 A | 6/1997 | Taheri ........................... 606/96 |
| 5,667,480 A | 9/1997 | Knight et al. ............... 600/210 |
| 5,667,520 A | 9/1997 | Bonutti ....................... 606/190 |
| 5,762,604 A | * 6/1998 | Kieturakis ................... 606/190 |
| 5,902,315 A | * 5/1999 | DuBois ....................... 606/190 |
| 6,068,639 A | * 5/2000 | Fogarty et al. ............. 606/190 |

* cited by examiner

Primary Examiner—Kevin Truong

(57) ABSTRACT

A dissector/retractor device comprising a balloon having a deflated state and an inflated state is described for performing minimally invasive surgical procedures by creating a tunnel alongside a target tissue in the body. The balloon in its inflated state forms an open space extending transversely through the balloon. The balloon is carried by an insertion assembly. The balloon may be an elongate torus shape with an elongate open area in its interior. The insertion assembly includes a blunt dissection device and a handle. In use, the dissector retractor is inserted through a small incision and bluntly tunneled through body tissue to a desired location. The balloon is inflated to create a space in the body tissue and may also dissect tissue as necessary away from the tissue to be treated. The balloon is left in place inflated to retract the space. Another incision may be made to provide more direct access to the target tissue than the original incision. The target tissue may then be diagnosed and/or treated through the direct access incision, through the overlying tissue and through the open space in the balloon.

12 Claims, 4 Drawing Sheets

APPARATUS AND METHOD FOR DISSECTING AND RETRACTING ELONGATE STRUCTURES

CROSS REFERENCE TO RELATED APPLICATIONS

This is a divisional of U.S. application Ser. No. 09/187,879; filed Nov. 6, 1998 now U.S. Pat. No. 6,179,854, which is a continuation-in-part of U.S. application Ser. No. 08/927,371, filed on Sep. 9, 1997 now U.S. Pat. No. 5,893,866, which is a continuation-in-part of U.S. application Ser. No. 08/815,398, filed on Mar. 10, 1997 now abandoned, which is a continuation-in-part of U.S. application Ser. No. 08/688,044, filed on Jul. 29, 1996 now abandoned, which is a continuation-in-part of U.S. application Ser. No. 08/447,124, filed on May 22, 1995 now U.S. Pat. No. 5,702,417. The priority of the prior applications are expressly claimed, and the disclosure of each of these prior applications is hereby incorporated by reference in its entirety.

FIELD OF THE INVENTION

This invention relates to methods and devices for endoscopic vascular surgery, in particular to methods and devices for dissecting tissue to create a working space adjacent an elongate structure.

BACKGROUND OF THE INVENTION

Surgical endoscopy is a surgical technique of using small diameter tools such as graspers, forceps, retractors, dissectors and clamps specially designed to be inserted through small openings in the body to perform operations within the body. The surgeon performing the surgery often cannot see the operation directly, and must watch the procedure on a video monitor fed by an endoscopic camera or through an endoscope. Endoscopic surgery may be preferable to open surgery because open surgery requires large incisions, essentially opening the body cavity completely in order to perform surgery deep within the body. The terms "laparoscopic surgery," and "arthroscopic surgery," are often considered to be types of endoscopic surgery, but are commonly used synonymously to refer to endoscopic surgery and minimally invasive surgery.

The surgeon performing such a surgery makes one, or a few, small incisions and inserts specially designed tools having small profiles through the incision and advances the tools to the desired location in the body. Long tools may be used to access over substantial distances from the incision deep into the body. Viewing the tools and the anatomy through an endoscope or on a video display from the endoscope, the surgeon can perform a wide variety of activities, including dissecting, retracting, cutting and suturing, necessary for a wide variety of surgical procedures.

In certain types of surgery dealing with elongate structures, for example blood vessels and long bones, it is desirable to dissect and/or retract tissue away from the elongate structure along at least a portion of their length. This may be accomplished in order to facilitate introduction of a tool or implant (temporary or permanent) alongside the structure, or to harvest at least a portion of the structure, such as a length of a vessel. In some instances, it may also be desirable to provide retraction of the tissue away from the elongate structure in the dissected region to create a working and/or a visualization space. In addition it is advantageous that the retraction be accomplished in a manner which minimizes blockage of surgical access to the dissected region thereby providing ample working and/or visualization space.

Many endoscopic surgical procedures may usefully employ such methods of dissecting and/or retracting tissue away from elongate structures. For example, in a blood vessel harvest, tissue is dissected away from the vessel and is then retracted to provide working and visualization space for ligating side branches and for completely separating the vessel from the surrounding tissue. Further, in the emergency treatment of long bone trauma, such as a fracture, it is often necessary to dissect along the bone to create space for plating. In both of these instances it is desirable to minimize the incision length, thereby accelerating the recovery process and its associated pain and reducing risk of infection. There are many inherent difficulties encountered in treating elongate structures using endoscopic techniques. For example, typically these procedures are performed through a single incision overlying one end of the region of the body to be treated. Hence, long tools must be used to reach from the incision site to the far end of the elongate structure being treated. In many situations, these long tools must navigate tortuous paths to reach the desired location in the body. These situations present several drawbacks in current methods. Firstly, it is difficult to advance long tools and to precisely position the distal end of the tools due to the extensive length of the tools and inherent visual uncertainty. Moreover, even after they are positioned, long tools are generally harder to maneuver and to operate than similar instruments having shorter lengths. Also, the long, narrow path to the desired location severely limits the maneuverability of the distal end of the instrument. This creates even greater difficulties and is especially undesirable where the orientation of the instrument is critical.

Many types of expanding devices which can be used to dissect and/or retract tissue for use in endoscopic procedures have been disclosed. A feature common to each of these devices is a small initial (or contracted or unexpanded) profile such that it can be inserted through a small incision. Once inserted, the device can be expanded to exert force on surrounding tissue to perform dissection and/or retraction. Further, the device must be capable of being contracted after use so that it can be removed through the same small incision. The designs of known devices varies greatly. For instance, devices have been disclosed which utilize mechanical means such as expanding arms, or inflatable apparatus which expands by pressurizing with fluid, or a combination of mechanical and inflatable mechanisms. For example, in commonly assigned U.S. Pat. Nos. 5,667,520 and 5,772,680 and U.S. application Ser. No. 08/927,371, the disclosures of which are hereby incorporated by reference in their entirety, various apparatus comprising mechanical, inflatable and combination mechanical/inflatable devices are disclosed which can be utilized to dissect and/or retract tissue. Depending on the nature of the application and surgical exposure desired, the apparatus are disclosed as having one or more expanding portions typically disposed on an insertion tool such as a blunt dissector or tunneling assembly, scope, rod, tube or other suitable structure. In many instances, an inflatable device provides superior performance because: (1) it can be contracted into a very small profile; (2) it is easily and variably expandable; (3) it can be readily formed into many different shapes specially designed for the particular procedure; (4) it can be made of transparent material to allow visualization through it; (5) the expansion force can be specifically and accurately directed to the desired tissue; and (6) the amount of force applied to the tissues can be precisely controlled.

In endoscopic procedures, an alternative to accessing the remote portions of a desired region of the body from the initial incision is to access the site from directly above the location. First, the region of interest in the body is dissected and/or retracted through an initial incision using the endoscopic techniques described above. Then, the surgeon locates the surface of the body directly above the site from the exterior of the body, such as by using the endoscope light which is often visible through the surrounding tissue. Finally, a small incision or puncture is made from directly above the site to the required depth. This method has the advantages that the surgeon is closer to the region of the body to be treated and relatively shorter instruments can be used. Furthermore, the shorter distance to the site of the procedure improves maneuverability and eases the use of the instruments. This method provides significant advantages with only a small increase in the total length of incisions.

The method of using additional incisions directly above the previously retracted region of an endoscopic surgery, however, requires that the retractors used provide direct access to the desired site from above. Although some of the inflatable retractors/dissectors described above are suitable for retracting elongate regions and can be inserted through small incisions and provide excellent dissection and retraction, they do not provide access through the overlying tissue and around or through the retractor. Instead, these prior elongate inflatable retractors/dissectors are configured to facilitate access along the path from the initial incision and therefore have solid surfaces which block direct access to the region from positions opposite the device. Although some of the previously disclosed inflatable devices described above are suitable for retracting elongate regions, none of the devices leaves adequate surgical access to the anatomy through and around the device.

Accordingly, there exists a need for an apparatus and corresponding method of using the apparatus which is suitable for dissecting and/or retracting elongate regions while also providing sufficient access to the region through overlying tissue and around or through the apparatus. Further, the apparatus should preferably be inflatable and adapted for use in endoscopic surgery.

SUMMARY OF THE INVENTION

The methods and devices of the present invention allow surgeons to endoscopically dissect and/or retract elongate regions in the body while also providing access to the region to be treated through the overlying tissue and through or around the device. The methods and devices disclosed herein permit elongate structures, such as the saphenous vein for example, to be effectively dissected and retracted from the surrounding tissues through a small incision at one end of the structure. In addition, access to the dissected and/or retracted region is made available through the overlying tissue and through or around the dissector/retractor device.

In an exemplary embodiment, a dissector/retractor of the present invention comprises an elongate balloon which in plan view has an interior open space through the balloon. For example, the balloon in its inflate state may be in the shape of an elongated ring or torus stretched so that it is no longer round in plan view but is instead oval or rectangular with rounded corners. The balloon may be formed of an elastic or non-elastic material. The balloon material may be transparent or substantially transparent to allow visualization or illumination through the balloon. An inflation harness is connected to the balloon and provides a fluid passageway into the interior space of the balloon.

The balloon may have a plurality of open spaces, especially if the balloon is very long. In that case, the balloon has at least one cross member which separates the open spaces and provides structural support to maintain the open spaces (similar to the steps on a ladder).

The balloon is carried by an insertion tool or assembly which facilitates advancing the balloon through an incision and into the body with dissection if needed to the target location. The insertion assembly preferably comprises a guide rod or blunt dissector. Alternatively, the insertion assembly may be a scope, a tube or other suitable support member. The balloon is preferably equipped with colinear tubular support members through which the insertion tool is inserted. The two support members are best positioned on opposite sides of the open space in the balloon so as to tether opposing portions of the elongate balloon. The support members may be integral parts of the balloon, or they may be separate parts which are attached to the balloon by adhesive, heat sealing, press fitting or other suitable attachment method.

In another aspect of the invention, a spoon-shaped blunt dissector may be attached to the distal end of the insertion tool or assembly or to the distal support member. The spoon extends beyond the distal end of the insertion tool. The spoon can be used to perform blunt dissection and/or retraction to tunnel the dissector/retractor into body tissue and to create an open space for viewing or for performing surgical procedures at the distal end of the dissector/retractor.

In another feature of the present invention, an optional balloon cover may be provided to retain the balloon with a small envelope in its uninflated state. The cover may be removeable or it may be permanently attached to the device. A resilient balloon cover may also be used which compresses the balloon upon deflation.

In still another aspect of the present invention, the dissector may have a handle at its proximal end. The handle preferably has an ergonomic design and is designed to fit comfortably in one hand of a surgeon, and to provide the surgeon greater control of the dissector during insertion and placement. The ergonomic handle may be adapted to receive and to provide supplementary support for a scope instrument, and can also hold a light source for the scope instrument.

In the general use of the dissector/retractor of the present invention, an incision is first made in the body at a location proximate the anatomy to be treated. The dissector/retractor is inserted through the incision with the balloon deflated, rolled and compacted. Where a scope is utilized, the entire method may be visualized. The dissector/retractor is advanced by tunneling into body tissue to where it is desired to dissect and retract body tissue to create a working space. Once the dissector/retractor is at the desired location, the balloon cover is removed from the balloon and the balloon is inflated. Upon inflation, the balloon expands. In many instances, inflation of the balloon will cause additional dissection of the surrounding tissue. If a larger dissected region is desired, multiple inflation, deflation and advancement cycles may be performed. The inflated balloon is left in place to maintain, i.e. retract, the dissected space. Then, another incision or puncture is made directly above the site of interest within the area just dissected and retracted. This incision provides direct access to the site without having to navigate along the path traveled by the dissector/retractor which may be a relatively long tunnel. The innovative configuration of the balloon has an interior open space which allows access to the desired site through the overlying tissue and through or around the balloon. Surgical instruments, diagnostic equipment and/or prosthesis may be inserted through the open space in the balloon to access the desired site of interest. Thus, a single device provides effective dissection and retraction along an elongate region of tissue thereby eliminating any need to remove a dissecting device and insert a different retracting device.

Moreover, if it is desired to perform surgical procedures on nearby regions of tissue, the balloon may be deflated and advanced further along the desired path by blunt dissection until the next desired location is reached. Then, the balloon may be reinflated. Another lateral incision may then be made to access the next region to be treated. These steps may be repeated as necessary.

After the treatment is complete, the balloon is deflated and the dissector/retractor is removed through the initial incision. The incisions are then closed so that they may heal.

Still further, at any time during the procedure, the insertion tool may be removed from the balloon and original incision by pulling it proximally from the support members. Then, other surgical apparatus may be inserted through the balloon.

A saphenous vein harvesting procedure will be described to exemplify the method of using the apparatus of the present invention for a specific procedure. It is to be understood that the above described method of the present invention may be used to perform many different surgeries and that this description is only illustrative and not limiting of the application of the methods disclosed herein. The surgeon makes one small incision at each end of the saphenous vein. After making the incisions, the surgeon inserts a dissector/retractor instrument which carries an elongate balloon having an interior open space. The surgeon advances or pushes the dissector/retractor along the saphenous vein to make a small tunnel adjacent the vein. When a side branch is encountered, the surgeon advances the device until the balloon open space is adjacent the junction. The surgeon then inflates the elongate balloon to enlarge the tunnel. The surgeon then makes another incision directly above the side branch to provide direct access to the side branch through the open space in the balloon. The surgeon inserts surgical instruments through the second incision and through the overlying tissue and through the open space in the balloon to divide and ligate the side branch to free the saphenous vein. The surgeon may also utilize a laparoscopic vein harvesting device, such as one of the hooked vein harvesting devices disclosed in co-pending U.S. application Ser. No. 08/444,424 entitled, "Methods and Devices for Blood Vessel Harvesting," into the leg to dissect the connective tissue from the vein. The disclosure of the aforementioned application Ser. No. 08/444,424 is hereby incorporated by reference in its entirety. After the vein is loosened and dissected free from its channel in the leg, the surgeon can cut the proximal and distal ends of the vein and easily pull the vein from the leg. These small skin incisions are then stitched so that they may heal. The small incisions heal much more readily, with fewer complications and far less pain, than the open procedures now in use.

The devices and methods of the present invention similarly may be effectively used in the placement of a prosthesis. The dissector/retractor is used to dissect along an elongate structure in the body similar to the method described above. The surgeon advances or pushes the dissector/retractor along the target structure until the desired location is reached. If an extended tunnel is desired, sequential inflation, deflation and advancement cycles may be performed to make a small tunnel along the bone. With the dissector/retractor at the desired location, the balloon is inflated to dissect and retract the tissue away from the target structure. The prosthesis is then put in place through the original incision. Alternatively, the insertion tool may be removed and the prosthesis can be inserted through the tubular support members. The surgeon then makes another incision directly above the side branch to provide direct access to the prosthesis. The surgeon then may adjust and/or affix the prosthesis to the target structure through the second incision and open space in the balloon. If necessary, the dissector/retractor can be deflated, advanced and reinflated to further adjust and/or affix the prosthesis through still another direct access incision. This procedure may be repeated as required.

Accordingly, it is an object of the present invention to provide improved methods and devices for performing minimally invasive surgery.

It is a further object of the present invention to provide an improved dissector/retractor having an elongate balloon with an open interior space and methods of using the same.

It is yet another object of the present invention to provide devices and methods for performing vein harvesting procedures.

It is still another object of the present invention to provide devices and methods for the placement of a prosthesis. Once the prosthesis is installed, the balloon is deflated and the dissector/retractor is removed. The procedure is completed by simply closing the small incisions.

DETAILED DESCRIPTION OF EXEMPLARY EMBODIMENTS

Figure 1:
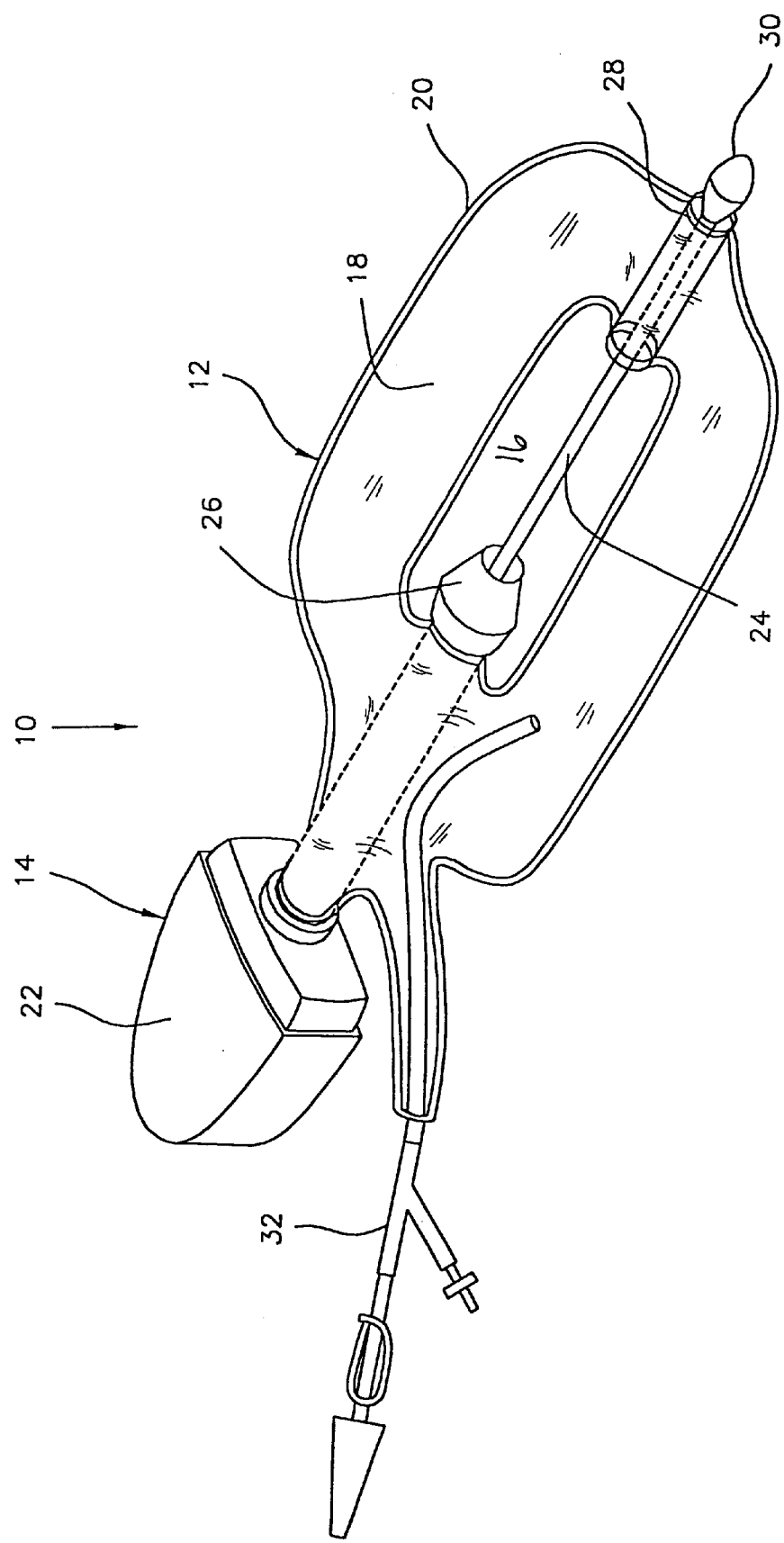
FIG. 1 is a perspective view of an exemplary embodiment of a dissector/retractor in accordance with the present invention.

Referring now to the drawings, FIG. 1 shows an exemplary embodiment of a dissector/retractor 10 according to the present invention. The dissector/retractor 10 comprises a balloon 12 (shown in FIG. 1 in an uninflated state) carried by an insertion device 14. The balloon 12 in an inflated state (see FIG. 2) forms an elongated torus (a surface generated by translating a substantially circular shape about an elliptical or rectangular path with curved corners) such that it has an interior open space 16. The balloon 12 is preferably formed of two sheets of material, a top sheet 18 and a bottom sheet 20, such that in its uninflated state, the balloon 12 can be compacted into a profile of small cross-section. It is contemplated that the balloon may have other suitable shapes depending on the intended surgical application so long as it has an adjacent or interior open space held open by the inflated balloon 12. For example, the cross-section of the inflated balloon 12 may other than round or elliptical. It may be square, oblong, triangular, elliptical, rectangular, "C" shaped, etc. Also, the balloon 12 may be formed to have alternative shapes in its inflated state, e.g. circular, square, elliptical, wedge-shaped, triangular, etc.

The balloon 12 may be made of inelastic, elastic, stretchable and/or non-stretchable material. For example, suitable balloon 12 materials include, but are not limited to, PVC, polyethylene, polyurethane, polyamide as well as latex or silicone.

The balloon 12 is equipped with two coaxial tubular support members 26 and 28 positioned on opposite sides of the open space 16. The support members 26 and 28 may be fixed to the balloon 12 by any suitable attachment method such as adhesive, heat sealing, press fitting, etc. Alternatively, the support members 26 and 28 may be formed integrally with the balloon 12.

The insertion device 14 comprises a handle 22 at its proximal end and a guide rod 24 (also called a blunt dissector or tunneling shaft) attached to the handle 22 and extending distally from the handle 22. The guide rod 24 is formed to have sufficient rigidity to bluntly dissect into tissue where no open space previously existed and may be made of surgical stainless steel or other suitable material. The guide rod 24 is inserted through the support members 26 and 28. The guide rod 24 may have a blunt tip 30 attached to its distal end or formed integrally with the guide rod 24.

A balloon inflation harness 32 extends from the balloon 12 and provides a fluid passageway into the interior of the balloon 12. The balloon inflation harness 32 is of the same type as that described in co-pending application Ser. No. 08/927,371, the disclosure of which is hereby incorporated by reference in its entirety, and therefore, it will not be described in detail herein. It should be appreciated that other suitable inflation devices are possible.

In another aspect of the present invention, the guide rod 24 may be replaced with an endoscope (not shown) which can serve as a blunt dissector. Alternatively, the guide rod 24 may be a hollow tube which receives an endoscope. The tube may be transparent or it may have openings through which the endoscope can view the surrounding anatomy. Using an endoscope affords the advantage of allowing visualization of the anatomy during use of the dissector/retractor 10.

In yet another feature of the present invention, a removeable balloon cover (not shown) may be provided to surround and compact the balloon 12 in its uninflated state. Suitable balloon covers, including perforated removable covers, are described in application Ser. No. 08/927,371 and are not described in detail herein. Moreover, the dissector/retractors of the present invention may have an ergonomic handle (not shown) such as those described in application Ser. No. 0/927,371. The ergonomic handle may further include a receptacle adapted to receive and support a standard scope and light source.

In a preferred method of use, an incision is made in the body proximate the target tissue within the body which is to be observed and/or treated. With the balloon 12 deflated, rolled and compacted around the insertion device 14, the dissector/retractor 10 is inserted through the incision. If a scope is utilized, the surrounding anatomy may be visualized during the procedure. The dissector/retractor 10 is advanced by pushing on the handle 22 to bluntly tunnel the dissector/retractor 10 through body tissue. Where it is desired to create a larger tunnel or a larger dissected area, the advancement of the dissector/retractor 10 is stopped and the balloon is inflated 12 causing it to expand (if a balloon cover is utilized, the cover is removed prior to inflation). In most instances, inflation of the balloon 12 will cause dissection of the surrounding tissue. Prior to continuing the advancement of the dissector/retractor 10, the balloon 12 is deflated. Once the open space 16 of the balloon 12 is adjacent the target tissue, the balloon 12 is inflated. The inflated balloon 12 is left in place to retract the previously dissected space.

Another incision is made directly above the location of the open space 16 of the balloon 12 thereby providing direct access to the area of the balloon without recourse to the tunnel just created by the dissector/retractor 10. Then, the surgeon may perform treatment on the site of interest through the direct access incision and through the open area 16 of the balloon 12.

If other regions of tissue need to be treated, the balloon 12 may be deflated and advanced to a new location. Then, the above step may be repeated to treat tissues in the new location. After treatment is complete, the balloon 12 is deflated and the dissector/retractor 10 is removed through the first incision.

Figure 2:
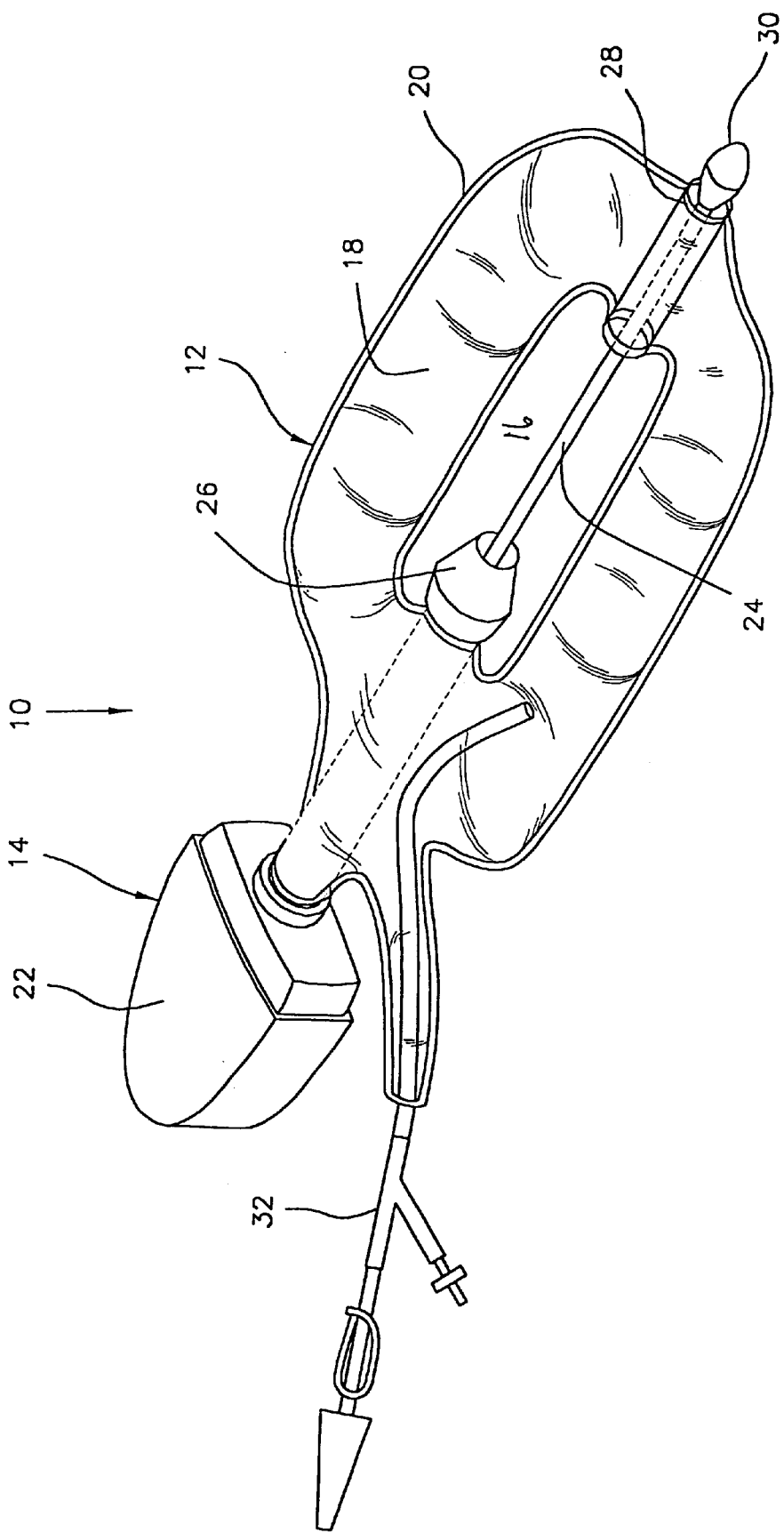
FIG. 2 is a perspective view of the dissector/retractor of FIG. 1 with the balloon in an inflated state.
Figure 3:
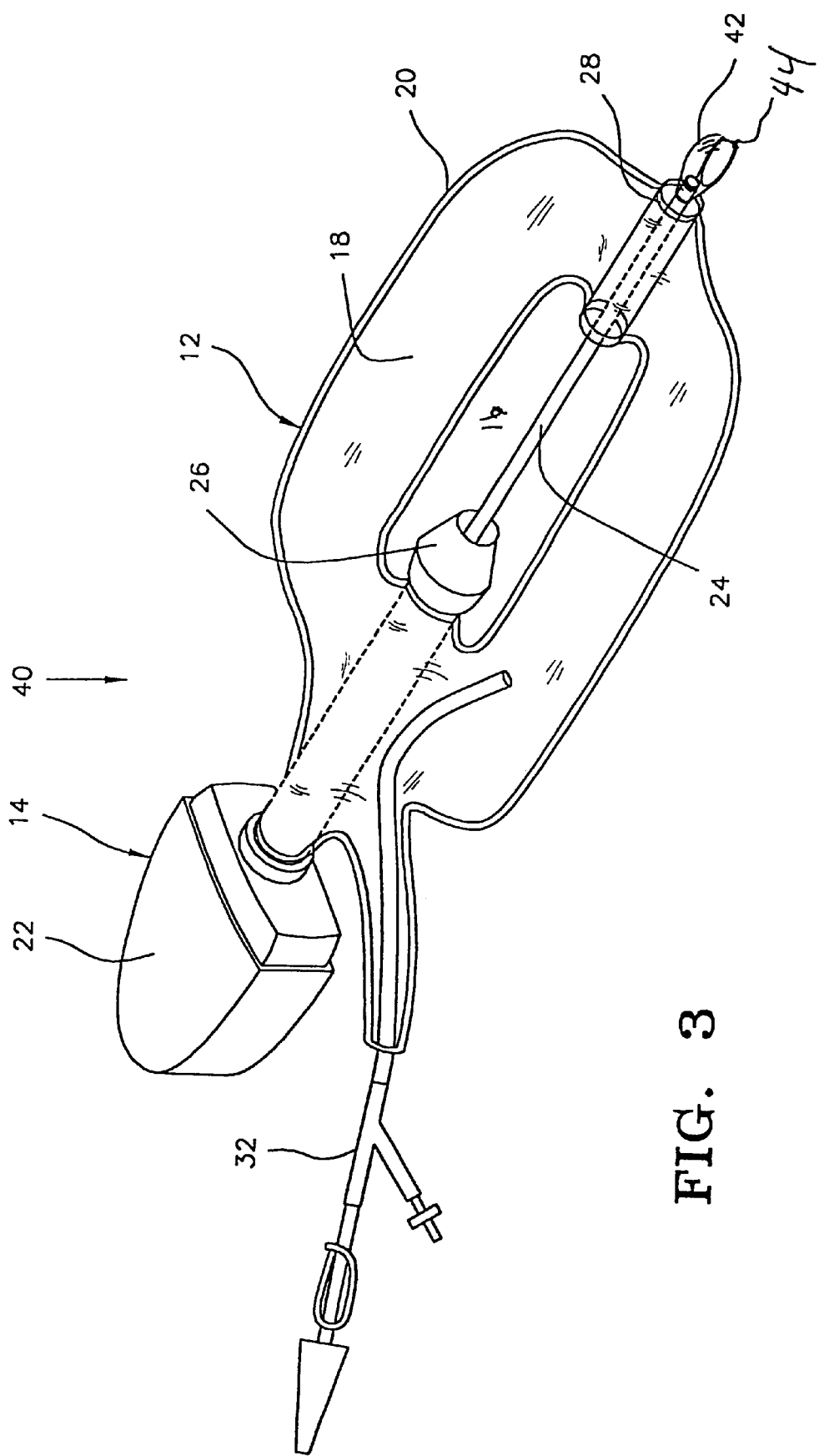
FIG. 3 is a perspective view of another exemplary embodiment of a dissector/retractor in accordance with the present invention.
Figure 4:
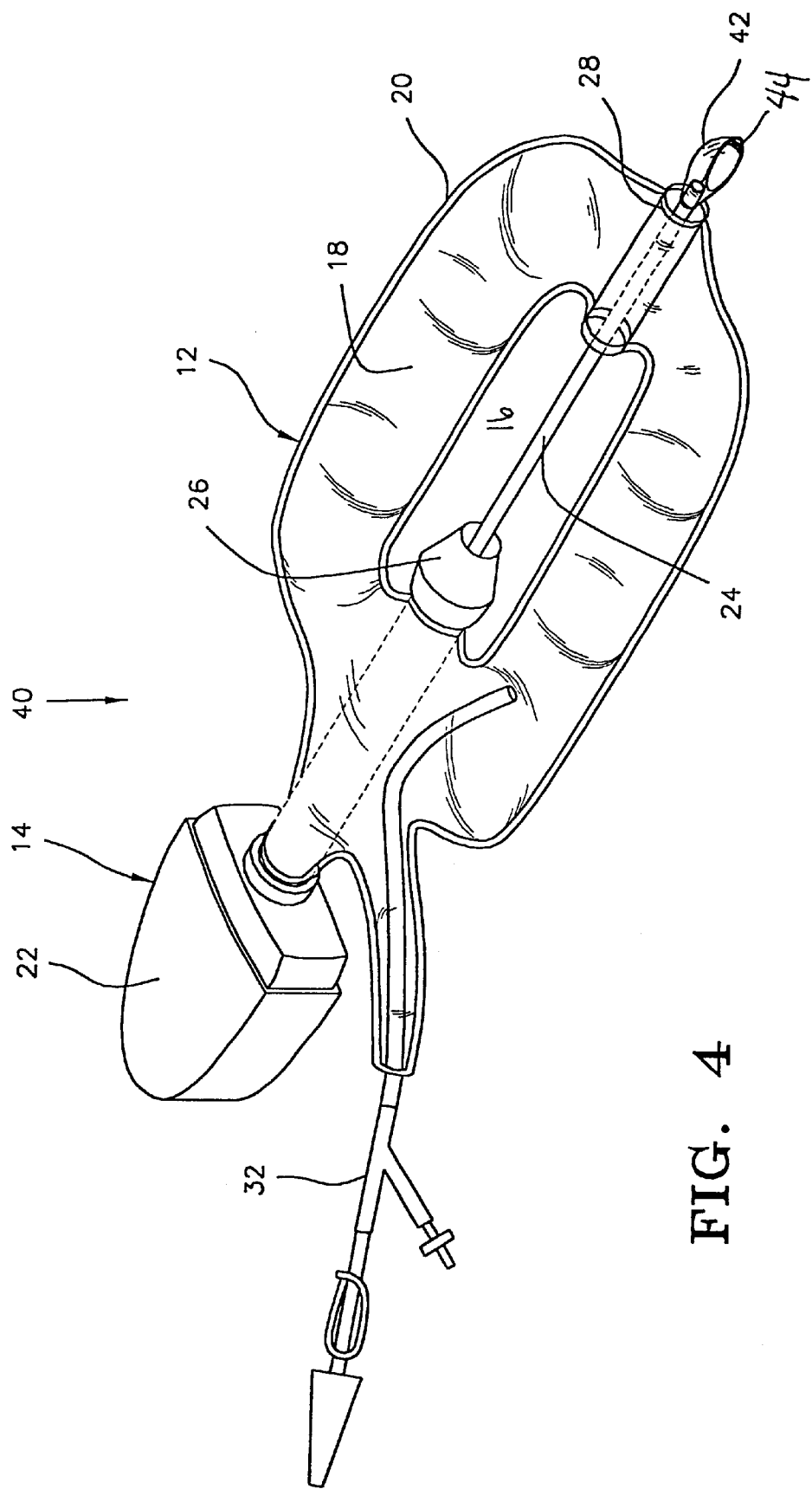
FIG. 4 is a perspective view of the dissector/retractor of FIG. 3 with the balloon in an inflated state.

Another exemplary embodiment of a dissector/retractor 40 according to the present invention is shown in FIGS. 2 and 3. The dissector/retractor 40 has a spoon-shaped dissector 42 attached to the distal end of the guide rod 24. Alternatively, the spoon-shaped dissector 42 may be attached to the distal end of the distal support member 28. In all other respects the dissector/retractor 40 is the same as the dissector/retractor 10 described above. Hence, throughout the drawings and description, like reference numerals refer to same or similar elements and therefore some elements may not be explicitly described for all figures. The spoon-shaped dissector is preferably translucent but may be transparent or opaque. The spoon-shaped dissector 42 may have a notch 44. The notch 44 is especially advantageous when dissecting along a blood vessel because the notch 44 straddles the vessel and helps prevent or reduce any undesired trauma to the vessel.

The method of using the dissector/retractor 40 is the same as that described above with respect to the dissector/retractor 10 of FIG. 1.

The devices and methods disclosed herein can be used for many surgical procedures including vein harvesting and plating bones as described above. It is to be understood that the specific descriptions of the devices and methods are intended to be illustrative only and that the devices and methods may be used for tunneling, enlarging and retracting working spaces over many different structures in the body. Various arteries and veins must be exposed and mobilized for operations other than harvesting, such as for poplitiel bypass, or a dialysis vein loop, or treating abnormal communicating vasculature.

Other structures, such as fallopian tubes, spermatic cords, bile ducts, and others may be dissected from surrounding tissue and treated similarly. These tissues may be dissected and treated using the devices and methods disclosed herein.

While the exemplary embodiments of the devices and methods have been described, they are merely illustrative of the principles of the invention. Other embodiments and configurations may be devised without departing from the spirit of the inventions and the scope of the appended claims.

Accordingly, the scope of the present invention should be determined not by the embodiments illustrated above, but by the appended claims and their legal equivalents.

What is claimed is:

1. A surgical apparatus comprising:
   an insertion assembly having a handle and a substantially rigid elongate member attached to said handle and extending distally from said handle; and
   an elongate balloon carried by said insertion assembly, said balloon having a deflated state and an inflated state, said balloon having an open space extending transversely through said balloon across a longitudinal axis of said insertion assembly.

2. The apparatus of claim 1 wherein said elongate balloon has an elongated torus shape.

3. The apparatus of claim 1 further comprising a blunt tip attached to a distal end of said elongate member.

4. The apparatus of claim 1 further comprising a spoon-shaped dissector attached to a distal end of said elongate member.

5. The apparatus of claim 4 wherein said spoon-shaped dissector has a notch in its distal end.

6. The apparatus of claim 1 further comprising a spoon-shaped dissector attached to a distal end of said insertion assembly.

7. The apparatus of claim 6 wherein said spoon-shaped dissector has a notch in its distal end.

8. The apparatus of claim 1 wherein said elongate member is a guide rod.

9. The apparatus of claim 1 wherein said elongate member is a tube.

10. The apparatus of claim 1 wherein said elongate member is an endoscope.

11. The apparatus of claim 1 further comprising at least one support member attached to said balloon, said at least one support member adapted to couple with said handle.

12. A surgical apparatus comprising:

an insertion assembly having a handle and a substantially rigid first elongate support member attached to said handle and extending distally from said handle, and a second elongate support member;

an elongate balloon carried by said insertion assembly and attached to said first and second support members, said balloon having a deflated state and an inflated state, said balloon in its inflated state having an open space extending transversely through said balloon and between said first and second support members; and a shroud having a proximal end and a distal section, the proximal end of the shroud being attached to a distal end of a rigid elongate member distally extendable from said handle through said first and second support members, the distal section of the shroud spaced apart from a distal end of said second support member to form an open space therebetween.

\* \* \* \* \*